United States Patent [19]

Carling et al.

[11] Patent Number: 5,763,448

[45] Date of Patent: Jun. 9, 1998

[54] PYRMIDINE DERIVATIVES

[75] Inventors: William Robert Carling, Bishops Stortford; Ian James Collins, Ware; Michael Rowley, Harlow, all of United Kingdom; Paul David Leeson, Monmouth Junction, N.J.

[73] Assignee: Merck, Sharp & Dohme Limited, Hoddesdon, England

[21] Appl. No.: 553,527

[22] PCT Filed: May 9, 1994

[86] PCT No.: PCT/GB94/00999

§ 371 Date: Mar. 18, 1996

§ 102(e) Date: Mar. 18, 1996

[87] PCT Pub. No.: WO94/26733

PCT Pub. Date: Nov. 24, 1994

[30] Foreign Application Priority Data

May 10, 1993 [GB] United Kingdom ............ 9309573

[51] Int. Cl.[6] ............... C07D 401/04; C07D 401/14; A61K 31/505

[52] U.S. Cl. .................. 514/274; 544/122; 544/123; 544/295; 544/296; 544/238; 544/316; 544/330; 544/331; 544/332; 544/333; 544/334; 544/335; 514/233.5; 514/235.8; 514/236.5; 514/252; 514/256; 514/275

[58] Field of Search ........................ 514/256, 274, 514/275, 233.5, 235.8, 236.5, 252; 544/316, 330, 331, 332, 333, 334, 335, 238, 123, 296

[56] References Cited

FOREIGN PATENT DOCUMENTS

| 0 168 262 | 1/1986 | European Pat. Off. . |
|---|---|---|
| 0 259 930 | 3/1988 | European Pat. Off. . |
| WO 85 00168 | 1/1985 | WIPO . |
| WO 94 10145 | 5/1994 | WIPO . |
| WO 94 10162 | 5/1994 | WIPO . |

OTHER PUBLICATIONS

Strekowski et al, Chemical Abstracts, vol. 117, abstract 204550 (1992).

Abdelal et al, Chemical Abstracts, vol. 117, abstract 111558 (1992).

Beilstein Reg. No. 6212885: Petrenko et al. Bull. Acad. Sci. vol. 29, No. 7, pp. 1154–1158 (1980).

*Primary Examiner*—John M. Ford
*Attorney, Agent, or Firm*—Melvin Winokur

[57] ABSTRACT

A class of substituted pyrimidine derivatives are ligands for dopamine receptor subtypes within the body and are therefore useful in the treatment of disorders of the dopamine system, in particular schizophrenia

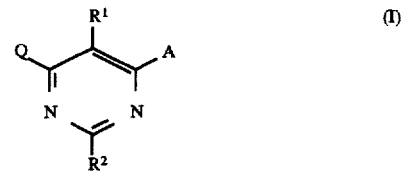

(I)

7 Claims, No Drawings

PYRIMIDINE DERIVATIVES

This is a national stage application filed under 35 USC §371 corresponding to international application PCT/GB94/00999, filed May 9, 1994.

This invention relates to a particular class of six-membered heteroaromatic compounds. More particularly, the invention is concerned with substituted pyrimidine derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system.

The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The compounds in accordance with the present invention, being ligands for dopamine receptor subtypes within the body, are accordingly of use in the treatment and/or prevention of disorders of the dopamine system.

The present invention accordingly provides a compound of formula I, or a salt thereof or a prodrug thereof:

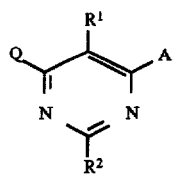

wherein

Q represents a substituted five- or six-membered monocyclic heteroaliphatic ring which contains one nitrogen atom as the sole heteroatom and is linked to the pyrimidine ring via a carbon atom;

$R^1$ represents hydrogen, halogen, $C_{1-6}$ alkyl, hydroxy or $C_{1-6}$ alkoxy;

$R^2$ represents hydrogen, halogen, $C_{1-6}$ alkyl, —$OR^a$ or —$NR^aR^b$; and

A represents a group of formula (i), (ii) or (iii):

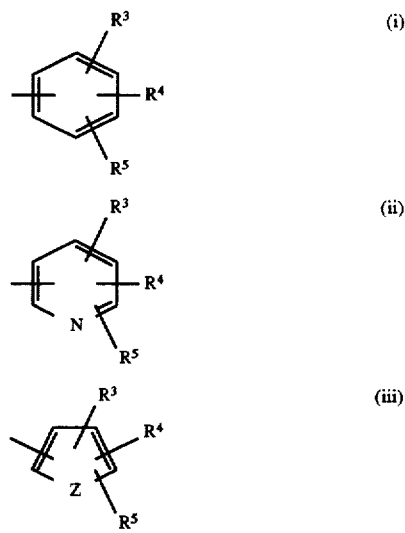

in which Z represents oxygen, sulphur or NH;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, $SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

The monocyclic heteroaliphatic ring Q in the compounds of formula I above represents a substituted pyrrolidinyl or piperidinyl moiety linked through carbon. Examples of suitable rings include the moieties of formula Qa to Qe:

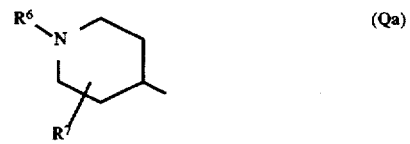

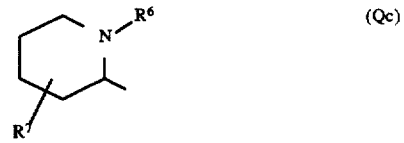

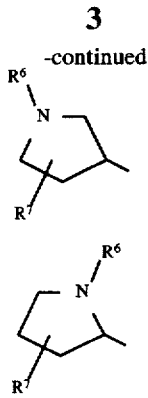

(Qd)

(Qe)

wherein one of $R^6$ and $R^7$ represents hydrocarbon or a heterocyclic group, and the other of $R^6$ and $R^7$ represents hydrogen, hydrocarbon or a heterocyclic group.

A particular monocyclic heteroaliphatic ring represented by the substituent Q in formula I is the ring of structure Qa above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl ($C_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl($C_{1-6}$)alkyl groups include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups.

Particular heteroaryl($C_{1-6}$)alkyl groups include pyridylmethyl and pyrazinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R", —NR"COR", —NR'CO$_2$R", —NR'SO$_2$R", —CH$_2$NR'SO$_2$R", —NHCONR'R", —CONR'R", —SO$_2$NR'R" and —CH$_2$SO$_2$NR'R", in which R' and R" independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituent $R^1$ represents hydrogen or $C_{1-6}$ alkyl, especially hydrogen or methyl.

Suitable values for the substituent $R^2$ include hydrogen, halogen, $C_{1-6}$ alkyl, hydroxy, $C_{1-6}$ alkoxy, amino, $C_{1-6}$ alkylamino and di($C_{1-6}$)alkylamino. Particular values of $R^2$ include chloro and amino.

Suitably, Z is sulphur.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, methoxy and chloro. Suitably, at least one of $R^3$, $R^4$ and $R^5$ is other than hydrogen.

Suitable values for the substituents $R^6$ and $R^7$ include $C_{2-6}$ alkenyl, $C_{3-7}$ cycloalkyl($C_{1-6}$)alkyl and aryl($C_{1-6}$)alkyl, any of which groups may be optionally substituted. In addition, one of $R^6$ and/or $R^7$ may represent hydrogen. Examples of suitable substituents on the groups $R^6$ and/or $R^7$ include $C_{1-6}$ alkyl, halogen, $C_{1-6}$ alkoxy, nitro and cyano.

Particular values of $R^6$ and $R^7$ include hydrogen, allyl, cyclopropylmethyl, cyclohexylmethyl, benzyl, methyl-benzyl, chlorobenzyl, dichlorobenzyl, methoxy-benzyl, nitro-benzyl, cyano-benzyl, naphthylmethyl, phenethyl and phenylpropyl, provided that at least one of $R^6$ and $R^7$ is other than hydrogen. Suitably, one of $R^6$ and $R^7$ represents hydrogen, and the other of $R^6$ and $R^7$ is other than hydrogen. Preferably, $R^7$ represents hydrogen and $R^6$ is other than hydrogen.

A particular sub-class of compounds according to the invention is represented by the compounds of formula IIA, and salts and prodrugs thereof:

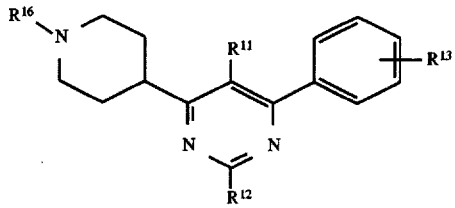
(IIA)

wherein $R^{11}$ represents hydrogen or $C_{1-6}$ alkyl;

$R^{12}$ represents hydrogen, halogen, $C_{1-6}$ alkyl, hydroxy, $C_{1-6}$ alkoxy, amino, $C_{1-6}$ alkylamino or di($C_{1-6}$)alkylamino;

$R^{13}$ represents hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl; and $R^{16}$ represents $C_{2-6}$ alkenyl, $C_{3-7}$ cycloalkyl($C_{1-6}$)alkyl or aryl($C_{1-6}$)alkyl, any of which groups may be optionally substituted.

Examples of suitable substituents on the group $R^{16}$ include one or more of $C_{1-6}$ alkyl, halogen, $C_{1-6}$ alkoxy, nitro and cyano.

Particular values of $R^{16}$ with reference to formula IIA above include allyl, cyclopropylmethyl, cyclohexylmethyl, benzyl, methyl-benzyl, chlorobenzyl, dichlorobenzyl, methoxy-benzyl, nitro-benzyl, cyano-benzyl, naphthylmethyl, phenethyl and phenylpropyl.

Suitably, $R^{11}$ represents hydrogen or methyl.

Suitable values of $R^{12}$ include hydrogen, halogen, $C_{1-6}$ alkyl, $C_{1-6}$ alkoxy and amino, especially chloro or amino.

Particular values of $R^{13}$ include hydrogen, chloro, methyl, ethyl, isopropyl and methoxy.

Another sub-class of compounds according to the invention is represented by the compounds of formula IIB, and salts and prodrugs thereof:

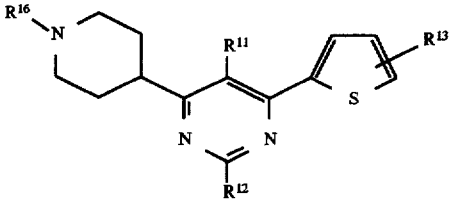
(IIB)

wherein $R^{11}$, $R^{12}$, $R^{13}$ and $R^{16}$ are as defined with reference to formula IIA above.

Specific compounds within the scope of the present invention include:

2-amino-4-(1-benzyl-4-piperidinyl)-6-(4-chlorophenyl) pyrimidine;

2-amino-6-(4-chlorophenyl)-5-methyl-4-[1-(2-phenylethyl) -4-piperidinyl]pyrimidine;

2-amino-5-methyl-6-phenyl-4-[1-(2-phenylethyl)--4- piperidinyl]pyrimidine;

2-chloro-5-methyl-6-phenyl-4-[1-(2-phenylethyl)-4- piperidinyl]pyrimidine;

2-amino-4-[1-(3-cyanobenzyl)-4-piperidinyl]-5-methyl-6- phenylpyrimidine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV or a salt thereof, e.g. the hydrochloride salt:

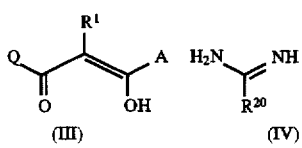

wherein Q, $R^1$ and A are as defined above, and $R^{20}$ corresponds to the group $R^2$ as defined above or represents a precursor group thereto; in the presence of a base; followed, where required, by conversion of the precursor group $R^{20}$ into the desired group $R^2$.

The reaction between compounds III and IV is conveniently carried out by heating the reactants in a suitable solvent, typically at the reflux temperature. The base employed will suitably be a $C_{1-4}$ alkoxide salt, in which case the reaction is conveniently effected in the corresponding $C_{1-4}$ alkanol as solvent. Typically, the reaction may be carried out in the presence of approximately two equivalents of sodium isopropoxide, utilising isopropanol as the solvent.

Where $R^2$ in the final product of formula I represents a group which is capable of being carried intact through the conditions of the reaction between compounds III and IV, for example $C_{1-6}$ alkyl or amino, then the substituent $R^{20}$ in the intermediates of formula IV will suitably correspond to the desired group $R^2$. Where, on the other hand, the group $R^2$ in the final product of formula I is a more reactive group, such as halogen, then the substituent $R^{20}$ in compound IV will advantageously represent a suitable precursor to the desired group $R^2$. By way of illustration, a product of formula I wherein $R^2$ is chloro will conveniently be obtained by reacting compound III with a compound of formula IV wherein $R^2$ is amino, and subsequently treating the compound of formula I wherein $R^2$ is amino thereby obtained with antimony trichloride and t-butyl nitrite, typically in dichloromethane at a temperature in the region of 0° C.

The compounds of formula III above may be prepared by reacting a carboxylic acid of formula V, or an activated derivative thereof, with two equivalents of a metal enolate of formula VI:

wherein $R^1$ and A are as defined above, $Q^1$ corresponds to the moiety Q as defined above or represents a precursor thereto protected on the nitrogen atom, and M represents a metal capable of providing a suitable counterion for the enolate anion; followed, where required, by removal of the N-protecting group from the moiety $Q^1$; and subsequently, if necessary, attachment to the nitrogen atom thereby deprotected of an appropriate substituent by standard means to afford a product containing the desired moiety Q.

For example, the substituent $Q^1$ in compound V may represent a moiety of formula Qa to Qe as defined above, in which $R^7$ is hydrogen and $R^6$ represents an N-protecting group. Once the reaction between compounds V and VI is complete the N-protecting group must be removed, and the desired group $R^6$ subsequently attached, by conventional methods.

The metal M is suitably an alkali metal, especially lithium.

The activated derivative of the carboxylic acid V is suitably the compound formed by reaction between the carboxylic acid V and 1,1'-carbonyldiimidazole, conveniently in tetrahydrofuran.

Where the substituent $Q^1$ represents a precursor to the moiety Q protected on the nitrogen atom, the N-protecting group is suitably an alkoxycarbonyl moiety such as t-butoxycarbonyl (BOC), in which case the N-protecting group can conveniently be removed subsequently as necessary by treatment under acidic conditions, e.g. stirring in hydrochloric acid or trifluoroacetic acid.

The reaction between compound V, or the activated derivative thereof, and compound VI is suitably carried out in a solvent such as tetrahydrofuran, commencing at –78° C. with warming to room temperature.

The metal enolate of formula VI is ideally prepared by reacting the corresponding carbonyl compound of formula VII:

wherein R and A are as defined above; with a non-nucleophilic base such as lithium diisopropylamide, suitably in tetrahydrofuran at –78° C.

Where they are not commercially available, the starting materials of formula IV, V and VII may be prepared by standard methods well known from the art.

It will be appreciated that any compound of formula I initially obtained from any of the above processes may, where appropriate, subsequently be elaborated into a further desired compound of formula I using techniques known from the art. For example, as noted above, a compound of formula I wherein $R^2$ is amino initially obtained may be converted into a compound of formula I wherein $R^2$ is chloro by treatment with antimony trichloride and t-butyl nitrite, typically in dichloromethane at a temperature in the region of 0° C.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (–)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[³H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50.000 for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [³H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [3 H]-spiperone from the human dopamine $D_4$ receptor subtype of below 1.5 μM.

EXAMPLE 1 a) 4-[1-(1,3-Dioxo-3-phenyl-2-methylpropyl)]piperidine hydrochloride

A solution of n-butyllithium in hexanes (1.6M, 125 cm³) was added at 10° C. to a stirred solution of diisopropylamine (28 cm³) in dry tetrahydrofuran (300 cm³) under an argon atmosphere. The resulting solution of lithium diisopropylamide was cooled to −78° C. and propiophenone (26 cm³) was added dropwise. The solution was stirred at −78° C. for 1 hour. Meanwhile, 1,1-carbonyldiimidazole (17.0g) was added portionwise at 0° C. to a stirred solution of 1-tert-butyloxycarbonylpiperidine-4-carboxylic acid (23.0g) in dry tetrahydrofuran (200 cm³).

Moderate effervescence was observed as the solids dissolved to form a pale yellow solution. The solution was transferred via cannula to the enolate solution, cooled to −78° C. The resulting thick, white suspension was stirred at −78° C. for 45 minutes and then warmed to room temperature. The suspension was poured into saturated aqueous ammonium chloride (500 cm³) and the mixture was extracted with ethyl acetate (2×200 cm³). The combined organic phases were dried ($MgSO_4$), filtered and concentrated to give a yellow oil. The oil was redissolved in ethyl acetate (100 cm³) and an ice-cold saturated solution of hydrogen chloride in ethyl acetate (200 cm³) was added. The resulting suspension was cooled to 4° C. for 24 hours. The solvent volume was reduced to 100 cm3 by evaporation, producing a white solid.

The solid was collected and dried at room temperature in vacuo to give the title compound (21.0 g, 75%); $\delta_H$ (360 MHz; $d_6$-DMSO) 1.26 (3H, d, J 7, $CH_3$), 1.53–1.63 (2H, m, 2×$NCH_2CH_AH_B$), 1.90–2.05 (2H, m, 2×$NCH_2CH_AH_B$), 2.82–2.94 (3H, m, 2×$NCH_AH_B$ and $NCH_2CH_2CH$), 3.02–3.08 (2H, m, 2×$NCH_AH_B$), 5.13 (1H, q, J 7, COCH($CH_3$)CO], 7.58 (2H, dd, J 7.5 and 7.5, 2×$ArH_{m\ to\ CO}$), 7.68 (1H, m, $ArH_{p\ to\ CO}$), 8.01 (2H, d, J 7.5, 2×$ArH_{o\ to\ CO}$), 9.11 and 9.34 (1H and 1H, 2×broad s, $^+NH_2$); m/z (CI⁺; $NH_3$)246 (M⁺+H; 100%).

b) 1-(2-Phenylethyl)-4-[1-(1,3-dioxo-3-phenyl-2-methylpropyl)piperidine hydrochloride 4-[1-(1,3-Dioxo-3-phenyl-2-methylpropyl)]piperidine hydrochloride (10.0 g) was partitioned between aqueous potassium carbonate (1M, 50 cm³) and dichloromethane (2×100 cm³). The organic extracts were dried ($MgSO_4$) filtered and concentrated to give the free base as a yellow oil. The oil was redissolved in dry dimethylformamide (200 cm³) and 1-(2-bromoethyl)benzene (5.3 cm³) and triethylamine (5.2 cm³) were added. The solution was heated at 50° C. under an argon atmosphere for 18 hours. The solution was cooled to room temperature and poured into saturated aqueous sodium hydrogen carbonate (500 cm³) prior to extraction with diethyl ether (2×200 cm³). The combined organic extracts were dried ($MgSO_4$), filtered and concentrated. The resulting yellow oil was redissolved in ethyl acetate (50 cm³) and a saturated solution of hydrogen chloride in ethyl acetate (150 cm³) was added. Solvent was removed by evaporation and the residues were triturated with diethyl ether to give the title compound as a white solid (9.95 g, 72%); $\delta_H$ (360MHz; $d_6$-DMSO) 1.27 (3H, d, J 7, $CH_3$), 1.80–2.10 (4H, m, 2×$NCH_2CH_2$), 2.84–3.29 (7H, m, 2×$NCH_AH_B$, $NCH_2CH_2Ph$ and $NCH_2CH_2CH$), 3.55–3.58 (2H, m, 2×$NCH_AH_B$), 5.17 [1H, q, J 7, COCH($CH_3$)CO], 7.21–7.35 (5H, m, Ph), 7.58 (2H, dd, J 7.5 and 7.5, 2×$ArH_{m\ to\ CO}$), 7.70 (1H, t, J 7.5, $ArH_{p\ to\ CO}$) and 8.03 (2H, d, J 7.5, 2×$ArH_{o\ to\ CO}$); m/z (CI⁺; $NH_3$) 350 (M⁺+H; 100%).

c) 2-Amino-4-f1-(2-phenylethyl)-4-piperidinyl]-6-phenyl-5-methylpyrimidine

A mixture of sodium (0.18 g) and dry propan-2-ol (15 cm³) was heated at reflux under an argon atmosphere until the sodium had dissolved. The solution was cooled and guanidine hydrochloride (0.74 g) was added. The suspension was heated at reflux for 1 hour and then cooled to room temperature. Meanwhile, 1-(2-phenylethyl)-4-[1-(1,3-dioxo-3-phenyl-2-methylpropyl)]piperidine hydrochloride (3.00 g) was partitioned between aqueous potassium carbonate (1M, 50 cm³) and dichloromethane (2×50 cm³). The combined organic extracts were dried ($MgSO_4$), filtered and concentrated to give the free base as a yellow oil. The oil was redissolved in dry propan-2-ol (5 cm³) and the solution was added to the previously prepared suspension. The mixture was heated at reflux under argon for 1.5 hours and was then diluted with water (20 cm³) and cooled to 0° C. The resulting white solid was collected. The material was recrystallised from ethanol-water to give the title compound (0.90 g, 31%) as white crystals, m.p. 199°–200° C. Found: C, 77.72; H, 7.48; N, 14.86. $C_{24}H_{28}N_4$ requires C, 77.38; H, 7.58; N, 15.04%. $\delta_H$ (360 MHz; $d_6$-DMSO) 1.65 (2H, apparent d, J 12, 2×$NCH_2CH_AH_B$), 1.84 (2H, apparent q, J 12, 2×$NCH_2CH_AH_B$), 2.02–2.08 (5H, m, 2×$NCH_AH_B$ and $CH_3$), 2.54 (2H, t, J 8, $NCH_2CH_2Ph$), 2.74–2.78 (3H, m, $NCH_2CH_2Ph$ and $NCH_2\ NCH_AH_B$), 6.23 (2H, broad s, $NH_2$), 7.16–7.30 (5H, m, Ph) and 7.41–7.44 (5H, m, Ph); m/z (CI⁺; $NH_3$) 373 (M⁺+H; 100%).

EXAMPLE 2

2-Chloro-4-[1-(2-phenylethyl)-4-piperidinyl]-6-phenyl-5-methylpyrimidine

A solution of antimony (III) chloride (0.61 g) in dry dichloromethane (2 cm3) was added to a solution of 2-amino-4-[1-(2-phenylethyl)-4-piperidinyl]-6-phenyl-5-methylpyrimidine (0.5 g) in dry dichloromethane (13 cm³) at 0° C. under argon. The resulting white suspension was stirred vigorously while tert-butyl nitrite (90%, 0.75 cm³) was added dropwise. The mixture was stirred at 0° C. for 3.5 hours and then poured into saturated aqueous sodium hydrogencarbonate solution (25 cm³). The mixture was diluted with dichloromethane (25 cm³) and filtered.

The filtrate was separated and the aqueous layer was extracted with 10% methanol-dichloromethane (2×25 cm³).

The combined organic extracts were dried (MgSO₄), filtered and concentrated to give the crude 2-chloropyrimidine as a yellow solid (0.40 g, 75%).

A sample (0.10 g) of the crude material was recrystallised from ethanol-water to give the title compound (0.03 g) as a white powder, m.p. 170°–171° C. Found: C, 73.65; H, 6.67; N, 10.40. $C_{24}H_{26}N_3Cl+0.05(CH_3CH_2OH)$ requires C, 73.42; H, 6.72; N, 10.66%. $\delta_H$ (360MHz; $d_6$-DMSO) 1.77–1.86 (4H, m, 2×NCH₂CH₂), 2.01 (2H, apparent td, J 11 and 4, 2×NCH$_A$H$_B$), 2.29 (3H, s, CH₃), 2.55 (2H, t, J 8, NCH₂CH₂Ph), 2.77 (2H, t, J 8, NCH₂CH₂Ph), 2.96–3.02 (1H, m, NCH₂CH₂CH), 3.07 (2H, apparent d, J 11, 2×NCH$_A$H$_B$), 7.16–7.31 (5H, m, Ph) and 7.51–7.58 (5H, m, Ph); m/z (CI⁺; NH₃) 392 (M⁺+H; 100%).

EXAMPLE 3

2-Amino-4-[1-(2-phenylethyl)-4-piperidinyl]-6-(4-chlorophenyl)-5-methylprimidine White granules, m.p. 179°–180° C. (from DMF-water). Found: C, 70.62; H, 6.61; N, 13.58. $C_{24}H_{27}N_4Cl$ requires C, 70.83; H, 6.69; N, 13.77%. $\delta_H$ (360 MHz; $d_6$-DMSO) 1.65 (2H, apparent d, J 12, 2×NCH₂CH$_A$H$_B$), 1.83 (2H, apparent q, J 12, 2×NCH₂CH$_A$H$_B$), 2.02–2.08 (5H, m, CH₃ and 2×NCH$_A$H$_B$), 2.54 (2H, t, J 8, NCH₂CH₂Ph), 2.73–2.81 (3H, m, NCH₂CH₂Ph and NCH₂CH₂CH), 3.04 (2H, apparent d, J 11, 2×NCH$_A$H$_B$), 6.28 (2H, s, NH₂), 7.16–7.30 (5H, m, Ph) and 7.46–7.52 (4H, m, ArH); m/z (CI⁺; NH₃) 407 (M⁺+H; 100%).

EXAMPLE 4

2-Amino-4-(1-benzyl-4-piperidinyl)-6-(4-chlorophenyl)pyrimidine

White granules, m.p. 251–253 (from EtOH). [Found: C, 57.46; H, 5.53; N, 12.03. $C_{21}H_{25}N_4Cl_2+0.4(H_2O)$ requires C, 57.56; H, 5.67; N, 12.21%.]; $\delta_H$ (360 MHz; $d_6$-DMSO) 2.10–2.20 (4H, m, 2×NCH₂CH₂), 2.86–3.24 (3H, m, 2×NCH$_A$H$_B$CH₂ and NCH₂CH₂CH), 3.42–3.45 (2H, m, 2×NCH$_A$H$_B$CH₂), 4.32 and 4.49 (2H, 2×d, J 5, NCH₂Ph), 7.24 (1H, s, C=CH), 7.46–7.48 (3H, m, 3 of Ph), 7.62–7.72 (4H, m, 2 of Ph and 2×ArH$_{o\ to\ Cl}$), 8.15 and 8.23 (2H, 2×d, J 8, 2×ArH$_{m\ to\ Cl}$), 11.03 and 11.16 (1H, 2×broad s, ⁺NH); m/z (CI⁺; NH₃) 379 (M⁺+H; 100%).

EXAMPLE 5

2-Amino-4-[1-(3-cyanobenzyl)-4-piperidinyl]-5-methyl-6-phenylpyrimidine

White granules, m.p. 176° C. (from ethyl acetate/petrol 60–80). [Found: C, 74.98; H, 6.55, N, 17.86. $C_{24}H_{25}N_5$ requires C, 75.17; H, 6.57; N, 18.26%]; $\delta_H$ (360 MHz; $d_6$-DMSO) 1.64 (2H, m), 1.87 (2H, m), 2.05 (3H, s), 2.08 (2H, m), 2.80 (1H, m), 2.89 (2H, m), 3.56 (2H, s), 6.25 (2H, br, s), 7.54–7.76 (9H, m); m/z (CI⁺; NH₃) 384 (M⁺+H; 100%).

We claim:

1. A compound of formula I, or a pharmaceutically acceptable salt thereof:

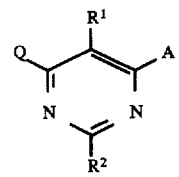

wherein

Q represents a substituted five- or six-membered monocyclic heteroaliphatic ring which contains one nitrogen atom as the sole heteroatom and is linked to the pyrimidine ring via a carbon atom;

R¹ represents hydrogen, halogen, $C_{1-6}$ alkyl, hydroxy or $C_{1-6}$ alkoxy;

R² represents hydrogen, halogen, $C_{1-6}$ alkyl, —OR$^a$ or —NR$^a$R$^b$; and

A represents a group of formula (i), (ii) or (iii):

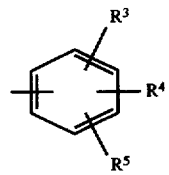

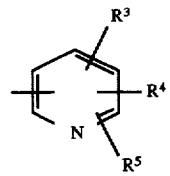

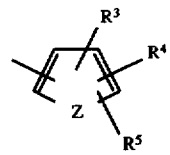

in which Z represents oxygen, sulphur or NH;

R³, R⁴ and R⁵ independently represent hydrogen, hydrocarbon, a heterocyclic group, halogen, cyano, trifluoromethyl, nitro, —OR$^a$, —SR$^a$, —SOR$^a$, SO₂R$^a$, —SO₂NR$^a$R$^b$, —NR$^a$R$^b$, —NR$^a$COR$^b$, —NR$^a$CO₂R$^b$, —COR$^a$, —CO₂R$^a$ or —CONR$^a$R$^b$; and R$^a$ and R$^b$ independently represent hydrogen, hydrocarbon or a heterocyclic group wherein said hydrocarbon is selected from the group consisting of: $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl and aryl ($C_{1-6}$)alkyl; wherein aryl is phenyl or naphthyl; and said heterocyclic group is selected from the group consisting of: $C_{3-7}$ heterocycloalkyl, $C_{3-7}$ heterocycloalkyl ($C_{1-6}$) alkyl, heteroaryl and heteroaryl ($C_{1-6}$) alkyl groups; wherein said heterocycloalkyl is selected from the group consisting of: azetidinyl, pyrrolidyl, piperidyl, piperazinyl and morpholinyl; and said heteroaryl group is selected from the group consisting of: pyridyl, quinolyl, isoquinolyl, pyridazinyl, pyrimidinyl, pyrazinyl, pyranyl, furyl, benzofuryl, dibenzofuryl, thienyl, benzthienyl, imidazolyl, oxadiazolyl and thiadiazolyl groups; wherein the hydrocarbon and heterocyclic groups can be substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl $(C_{1-6})$alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R'', —NR''COR''', —NR''CO$_2$R''', —NR''SO$_2$R''', —CH$_2$NR''SO$_2$R''', —NHCONR'R'', —CONR'R'', —SO$_2$NR'R'' and —CH$_2$SO$_2$NR'R'', in which R' and R'' independently represent hydrogen, $C_{1-6}$ alkyl, aryl or aryl $(C_{1-6})$ alkyl.

2. A compound as claimed in claim 1 represented by formula IIA, and salts thereof:

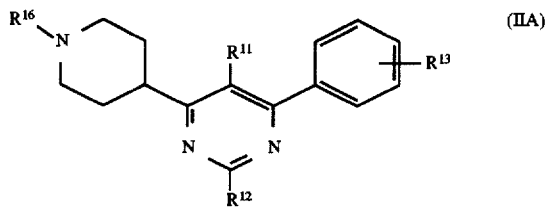

wherein $R^{11}$ represents hydrogen or $C_{1-6}$ alkyl;

$R^{12}$ represents hydrogen, halogen, $C_{1-6}$ alkyl, hydroxy, $C_{1-6}$ alkoxy, amino, $C_{1-6}$ alkylamino or di($C_{1-6}$) alkylamino;

$R^{13}$ represents hydrogen, halogen, cyano, nitro, trifluoromethyl, amino, $C_{1-6}$ alkylamino, di($C_{1-6}$) alkylamino, $C_{1-6}$ alkyl, $C_{1-6}$ alkoxy, aryl($C_{1-6}$)alkoxy or $C_{2-6}$ alkylcarbonyl; and $R^{16}$ represents $C_{2-6}$ alkenyl, $C_{3-7}$ cycloalkyl($C_{1-6}$)alkyl or aryl $(C_{1-6})$alkyl, any of which groups can be substituted with one or more of $C_{1-6}$ alkyl, halogen, $C_{1-6}$ alkoxy, nitro and cyano.

3. A compound as claimed in claim 2 wherein $R^{13}$ represents hydrogen, chloro, methyl, ethyl, isopropyl or methoxy.

4. A compound as claimed in claim 2 wherein $R^{16}$ represents allyl, cyclopropylmethyl, cyclohexylmethyl, benzyl, methyl-benzyl, chlorobenzyl, dichlorobenzyl, methoxy-benzyl, nitro-benzyl, cyano-benzyl, naphthylmethyl, phenethyl or phenylpropyl.

5. A compound as claimed in claim 1 selected from:

2-amino-4-(1-benzyl-4-piperidinyl)-6-(4-chlorophenyl) pyrimidine;

2-amino-6-(4-chlorophenyl)-5-methyl-4-|1-(2-phenylethyl) -4-piperidinyl]pyrimidine;

2-amino-5-methyl-6-phenyl-4-[1-(2-phenylethyl)-4-piperidinyl]pyrimidine;

2-chloro-5-methyl-6-phenyl-4-[1-(2-phenylethyl)-4-piperidinyl]pyrimidine;

2-amino-4-[1-(3-cyanobenzyl)-4-piperidinyl]-5-methyl-6-phenylpyrimidine;

and salts thereof.

6. A pharmaceutical composition comprising a compound as claimed in claim 1 in association with a pharmaceutically acceptable carrier.

7. A method for the treatment of schizophrenia which comprises administering to a patient in need of such treatment an effective amount of a compound as claimed in claim 1.

* * * * *